(12) United States Patent
Hatano et al.

(10) Patent No.: US 9,296,700 B2
(45) Date of Patent: Mar. 29, 2016

(54) METHOD FOR PURIFYING A PYRAZOLINONE DERIVATIVE

(75) Inventors: Ryo Hatano, Ibaraki (JP); Sosuke Miyaoka, Tokyo (JP); Shinsuke Abe, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 9 days.

(21) Appl. No.: 13/320,281

(22) PCT Filed: Jun. 1, 2010

(86) PCT No.: PCT/JP2010/059585
§ 371 (c)(1),
(2), (4) Date: Nov. 14, 2011

(87) PCT Pub. No.: WO2010/143598
PCT Pub. Date: Dec. 16, 2010

(65) Prior Publication Data
US 2012/0071666 A1    Mar. 22, 2012

(30) Foreign Application Priority Data
Jun. 8, 2009 (JP) ................................ 2009-136995

(51) Int. Cl.
*C07D 231/52* (2006.01)

(52) U.S. Cl.
CPC .................................... *C07D 231/52* (2013.01)

(58) Field of Classification Search
None
See application file for complete search history.

(56) References Cited

U.S. PATENT DOCUMENTS

| 6,294,567 B1 | 9/2001 | Hashizume et al. |
| 2002/0137944 A1 | 9/2002 | Fukae |
| 2005/0075508 A1 | 4/2005 | Fukae et al. |
| 2006/0149098 A1 | 7/2006 | Fukae et al. |

FOREIGN PATENT DOCUMENTS

| EP | 2186802 A1 | 5/2010 |
| JP | 2000-226374 A | 8/2000 |
| JP | 2007-302619 A | 11/2007 |
| JP | 2008-049304 A | 3/2008 |
| WO | 2009020203 A1 | 2/2009 |

OTHER PUBLICATIONS

Int'l Search Report issued Jun. 29, 2010 in Int'l Application No. PCT/JP2010/059585.
Uusi-Penttila et al, "Spectroscopic monitoring of environmentally benign anti-solvent crystallization," Journal of Crystal Growth, vol. 166, pp. 967-970 (1996).
Int'l Prelminary Report on Patentability issued Jan. 26, 2012 in Int'l Application No. PCT/JP2010/059585.
Supplementary Search Report issued Oct. 23, 2012 in EP Application No. 10786129.6.
Office Action issued Aug. 25, 2013 in IL Application No. 216503.
Office Action issued Aug. 28, 2013 in CN Application No. 201080024419.0.
Tung et al, "Crystallization of Organic Compounds: An Industrial Perspective," John Wiley & Sons, pp. 179-181 (2009).
Office Action issued Apr. 2, 2014 in Chinese Application No. 201080024419.0.
Office Action issued Oct. 10, 2014 in CN Application No. 201080024419.0.
Decision of Refusal issued Jun. 23, 2014 in JP Application No. 2010-124105.
Office Action issued May 9, 2014 in TW Application No. 099117933.
Office Action issued Sep. 5, 2014 in TW Application No. 099117933.
Office Action issued Apr. 8, 2014 in JP Application No. 2010-124105.
"New Experimental Chemistry Lecture 1, Basic Operations I," Maruzen Co., Lotd., pp. 296-304, Mar. 20, 1978 (English translation of relevant portion attached).

*Primary Examiner* — Alicia L Otton
(74) *Attorney, Agent, or Firm* — Panitch Schwarze Belisario & Nadel LLP

(57) ABSTRACT

A method for purifying a pyrazolinone derivative comprising a step of mixing a solution containing a mixture containing the pyrazolinone derivative and a good solvent which can dissolve the pyrazolinone derivative with a poor solvent to crystallize the pyrazolinone derivative.

5 Claims, No Drawings

METHOD FOR PURIFYING A PYRAZOLINONE DERIVATIVE

CROSS-REFERENCE TO RELATED APPLICATION

This application is a Section 371 of International Application No. PCT/JP2010/059585, filed Jun. 1, 2010, which was published in the Japanese language on Dec. 16, 2010, under International Publication No. WO 2010/143598 A1, and the disclosure of which is incorporated herein by reference.

TECHNICAL FIELD

The present invention relates to a method for purifying a pyrazolinone derivative.

BACKGROUND ART

Pyrazolinone derivatives such as 1-[(2-propenylthio)carbonyl]-4-(2-methylphenyl)-5-amino-1H-pyrazol-3-one are known to be effective for controlling plant diseases. As a method for purifying the derivative, a method for purifying a mixture containing the derivative by column chromatography is described in Patent Document 1.

[Patent Document 1] Japanese Unexamined Patent/Application Publication No. 2000-226374

SUMMARY OF THE INVENTION

The above purifying method by column chromatography is, however, not necessarily industrially easy, and a method, other than the above, for industrially easily purifying a pyrazolinone derivative is demanded.

Under such situation, the present inventors led to the invention described below.

That is, the present invention is to provide the following [1] to [9].

[1]. A method for purifying a pyrazolinone derivative comprising a step of mixing a solution containing a mixture containing the pyrazolinone derivative represented by the formula (1) and a good solvent which can dissolve the pyrazolinone derivative with a poor solvent to crystallize the pyrazolinone derivative, Formula (1)

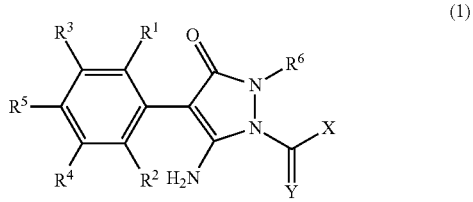

(1)

wherein $R^1$, $R^2$, $R^3$, $R^4$ and $R^5$ independently represent a hydrogen atom, a halogen atom, an alkyl group, a haloalkyl group, an alkoxy group, an alkoxyalkyl group, an alkoxyalkoxy group, a haloalkoxy group, an alkylthio group, a haloalkylthio group, a cyano group, a nitro group, an optionally substituted phenyl group, or an optionally substituted phenoxy group; or adjacent two of $R^1$, $R^2$, $R^4$ and $R^5$ together represent —CH=CH—CH=CH— or an alkylene group, and a carbon atom(s) contained in the —CH=CH—CH=CH— or alkylene group is(are) optionally replaced by an oxygen atom(s), and a hydrogen atom(s) contained in the —CH=CH—CH=CH— or alkylene group is(are) optionally substituted with a halogen atom(s) or an alkyl group(s); $R^6$ represents an optionally substituted alkyl group, an optionally substituted alkenyl group, an optionally substituted alkynyl group, an optionally substituted phenyl group or an optionally substituted alicyclic hydrocarbon group; X represents an optionally substituted alkyl group, an optionally substituted alkenyl group, an optionally substituted alkynyl group, an optionally substituted phenyl group, an optionally substituted alkoxy group, an optionally substituted alkenyloxy group, an optionally substituted alkynyloxy group, an optionally substituted phenoxy group, an optionally substituted alkylthio group, an optionally substituted alkenylthio group, an optionally substituted alkynylthio group, an optionally substituted phenylthio group, or an optionally substituted alicyclic hydrocarbon group; and Y represents an oxygen atom or a sulfur atom.

[2]. The purifying method as described in [1], wherein the good solvent is an aromatic hydrocarbon, and the poor solvent is at least one hydrocarbon selected from the group consisting of an aliphatic hydrocarbon and an alicyclic hydrocarbon.

[3]. The purifying method as described in [1] or [2], said method mixing to contain 1 to 50 parts by weight of the pyrazolinone derivative represented by the formula (1) per 100 parts by weight of the poor solvent.

[4]. The purifying method as described in any of [1] to [3], wherein the crystallization is carried out at −20° C. to 20° C.

[5]. The purifying method as described in any of [1] to [4], wherein the solution containing the mixture containing the pyrazolinone derivative represented by the formula (1) and the good solvent which can dissolve the pyrazolinone derivative was added to the poor solvent to crystallize the pyrazolinone derivative.

[6]. A method for purifying a pyrazolinone derivative comprising a step of mixing a solution containing a mixture containing the pyrazolinone derivative represented by the formula (1) and a good solvent which can dissolve the pyrazolinone derivative with a poor solvent to crystallize the pyrazolinone derivative, Formula (1)

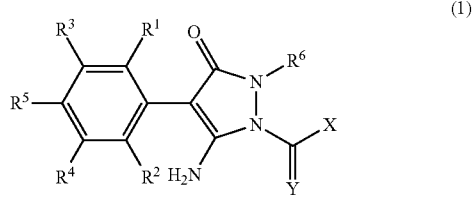

(1)

wherein $R^1$, $R^2$, $R^3$, $R^4$ and $R^5$ independently represent a hydrogen atom, a halogen atom, an alkyl group, a haloalkyl group, an alkoxy group, an alkoxyalkyl group, an alkoxyalkoxy group, a haloalkoxy group, an alkylthio group, a haloalkylthio group, a cyano group, a nitro group, an optionally substituted phenyl group, or an optionally substituted phenoxy group; or adjacent two of $R^1$, $R^2$, $R^3$, $R^4$ and $R^5$ together represent —CH=CH—CH=CH— or an alkylene group, and a carbon atom(s) contained in the —CH=CH—CH=CH— or alkylene group is(are) optionally replaced by an oxygen atom(s), and a hydrogen atom(s) contained in the —CH=CH—CH=CH— or alkylene group is(are) optionally substituted with a halogen atom(s) or an alkyl group(s); $R^6$ represents an optionally substituted alkyl group, an optionally substituted alkenyl group, an optionally substituted alkynyl group, an optionally substituted phenyl group or an optionally substituted alicyclic hydrocarbon group; X represents an optionally substituted alkyl group, an optionally substituted alkenyl group, an optionally substituted alkynyl group, an optionally substituted phenyl group, an optionally substituted alkoxy group, an optionally substituted alkenyloxy group, an optionally substituted alkynyloxy group, an optionally substituted phenoxy group, an optionally substituted alkylthio group, an optionally substituted alkenylthio group, an optionally substituted alkynylthio group, an optionally substituted phenylthio group, or an optionally substituted alicyclic hydrocarbon group; and Y represents an oxygen atom or a sulfur atom; said method comprising the following first step to third step, First step: a step of adding part of a solution containing a mixture containing a pyrazolinone derivative represented by the formula (1) and a good solvent which can dissolve the pyrazolinone derivative to a poor solvent to obtain a mixed liquid (1), Second step: a step of crystallizing the pyrazolinone derivative represented by the formula (1) contained in the mixed liquid (1) obtained in the first step to obtain a mixed liquid (2) containing crystals of the derivative, and Third step: a step of further adding the remaining part of said solution to the mixed liquid (2) obtained in the second step to crystallize the pyrazolinone derivative represented by the formula (1).

[7]. The purifying method as described in [6], wherein an amount of said solution to be used in the first step is 1 to 10 parts by weight per 100 parts by weight of the total of said solution to be used in the first step and said solution to be used in the third step.

[8]. The purifying method as described in any of [1] to [4], wherein the crystallization is carried out while stirring by a retreat curve agitator at a required power of 0.05 to 0.7 kW/m³.

[9]. The purifying method as described in [6] or [7], wherein the crystallization is carried out while stirring by a retreat curve agitator at a required power of 0.05 to 0.7 kW/m³ in the third step.

MODES OF CARRYING OUT THE INVENTION

The present invention comprises a step of crystallizing from a solution (hereinafter may be referred to as solution (2)) containing the above derivative represented by the formula (1) (hereinafter may be referred to as Derivative (1)) and a good solvent which can dissolve the Derivative (1), the Derivative (1).

In Derivative (1), examples of the halogen atom represented by $R^1$, $R^2$, $R^3$, $R^4$ or $R^5$ include a fluorine atom, a chlorine atom, a bromine atom, or an iodine atom; examples of the alkyl group include C1-C5 alkyl groups (such as a methyl group, an ethyl group, a n-propyl group, an isopropyl group and a tert-butyl group); examples of the haloalkyl group include C1-C5 haloalkyl groups (such as a trifluoromethyl group, a tetrafluoroethyl group, and a heptafluoropropyl group); examples of the alkoxy group include C1-C5 alkoxy groups (such as a methoxy group, an ethoxy group, a propyloxy group and an isopropyloxy group); examples of the alkoxyalkyl group include C1-C3 alkoxy C1-C3 alkyl groups (such as a methoxymethyl group); examples of the alkoxyalkoxy group include C1-C3 alkoxy C1-C3 alkoxy groups (such as a methoxymethoxy group); examples of the haloalkoxy group include C1-C5 haloalkoxy groups (such as a trifluoromethoxy group, a difluoromethoxy group and a tetrafluoroethoxy group); the alkylthio group includes C1-C5 alkylthio groups (such as a methylthio group and an ethylthio group); and examples of the haloalkylthio group include C1-C5 haloalkylthio groups (such as a trifluoromethylthio group).

In the present invention, Cn-Cm means n to m carbon atoms, for example, a C1-C5 alkyl group means an alkyl group having 1 to 5 carbon atoms.

The optionally substituted phenyl group means a phenyl group which optionally has 1 to 5 substituent(s), and the optionally substituted phenoxy group means a phenoxy group which optionally has 1 to 5 substituent(s).

Examples of substituents in the present invention can include halogen atoms (such as a fluorine atom, a chlorine atom, a bromine atom and an iodine atom); C1-C5 alkyl groups (such as a methyl group and an ethyl group); C1-C5 alkoxy groups (such as a methoxy group and an ethoxy group); C1-C5 alkylthio groups (such as a methylthio group and an ethylthio group); C1-C5 haloalkyl groups (preferably C1-C2 haloalkyl groups: such as a trifluoromethyl group); C1-C5 haloalkoxy groups (preferably C1-C2 haloalkoxy groups: such as a trifluoromethoxy group and a difluoromethoxy group); C1-C5 haloalkylthio groups (preferably C1-C2 haloalkylthio groups: such as a trifluoromethylthio group); and a cyano group.

In $R^1$, $R^2$, $R^3$, $R^4$ and $R^5$, adjacent two of these together represent —CH=CH—CH=CH— or an alkylene group (preferably C1-C6 alkylene groups, e.g. a trimethylene group (—(CH$_2$)$_3$—) and a tetramethylene group (—(CH$_2$)$_4$—)).

A carbon atom(s) contained in the —CH=CH—CH=CH— or alkylene group is(are) optionally replaced by an oxygen atom(s), and a hydrogen atom(s) contained in the —CH=CH—CH=CH— or alkylene group is(are) optionally substituted with a halogen atom(s) or an alkyl group(s).

Examples in which a carbon atom(s) contained in the alkylene group is(are) replaced by an oxygen atom(s) can include a methylenedioxy group (—O—CH$_2$—O—) and a group represented by —OCH$_2$CH$_2$—.

An example in which hydrogen atoms contained in the —CH=CH—CH=CH— or alkylene group are substituted with halogen atoms includes a difluoromethylenedioxy group (—O—CF$_2$—O—), and an example in which a hydrogen atom contained in the —CH=CH—CH=CH— or alkylene group is substituted with an alkyl group includes a group represented by —OCH$_2$CH(CH$_3$)—.

Among $R^1$, $R^2$, $R^3$, $R^4$ and $R^5$ in Derivative (1), a compound wherein 1 or more and 3 or less groups are a halogen atom(s) (especially a chlorine atom), an alkyl group(s) (especially a methyl group) or a haloalkyl group(s) (especially a trifluoromethyl group), and all of the rest is hydrogen atoms is preferred. Further, a compound wherein $R^3$, $R^4$ and $R^5$ are hydrogen atoms is more preferred.

In Derivative (1), examples of the optionally substituted alkyl group represented by $R^6$ can include C1-C10 alkyl groups (such as an ethyl group, a propyl group, an isopropyl group, a butyl group, an isobutyl group, a sec-butyl group, a tert-butyl group, a 1-methylbutyl group and a 1-ethylpropyl group), C1-C10 haloalkyl groups (such as a 1-methyl-2,2,2-trifluoroethyl group and 1-methyl-3-chloropropyl group), C1-C5 alkoxy C1-C5 alkyl groups (such as a 2-methoxyethyl group), C1-C5 alkylthio C1-C5 alkyl groups (such as a 2-methylthioethyl group), C1-C5 haloalkoxy C1-C5 alkyl groups (such as 1-methyl-(2,2,2-trifluoroethoxy)ethyl group and the like), C1-C5 haloalkoxy C1-C5 haloalkyl groups, C1-C5 haloalkylthio C1-C5 alkyl groups (such as a 1-methyl-(2,2, 2-trifluoroethylthio)ethyl group), C1-C5 haloalkylthio C1-C5 haloalkyl groups, cyano C1-C5 alkyl groups (such as a 1-cyanoethyl group), cyano C1-C5 haloalkyl groups (such as a 1-cyano-2,2,2-trifluoroethyl group), C1-C5 alkoxycarbonyl C1-C5 alkyl groups (such as a 1-(methoxycarbonyl) ethyl group), C1-C5 alkyl groups substituted with a C3-C8 alicyclic hydrocarbon group which optionally has halogen atoms and optionally contains unsaturated bonds (such as a 1-cyclopropylethyl group), or C7-C17 aralkyl groups which optionally have 1 to 5 substituent(s) (such as a benzyl group, an α-methylbenzyl group and an α,α-dimethylbenzyl group).

Examples of the optionally substituted alkenyl group represented by $R^6$ can include C2-C10 alkenyl groups (such as a 1-methyl-2-propenyl group), and C2-C10 haloalkenyl groups (such as a 2-chloro-1-methyl-2-propenyl group), examples of the optionally substituted alkynyl group can include C2-C10 alkynyl groups (such as a 1-methyl-2-propynyl group), and C2-C10 haloalkynyl groups (such as a 1-methyl-2-chloro-3-butynyl group), and examples of the optionally substituted alicyclic hydrocarbon group can include C3-C8 alicyclic hydrocarbon groups which optionally have halogen atoms and which optionally contain unsaturated bonds (such as a cyclopentyl group and a cyclohexyl group).

Examples of the optionally substituted phenyl group represented by $R^6$ can include a phenyl group and the like.

In Derivative (1), examples of the optionally substituted alkyl group represented by X can include C1-C10 alkyl groups (preferably C1-C5 alkyl groups: such as a methyl group, an ethyl group, a propyl group, an isopropyl group, a butyl group, an isobutyl group, a sec-butyl group, a 2-methylbutyl group, an isopentyl group and a tert-butyl group), C1-C10 haloalkyl groups (such as a trifluoromethyl group, a tetrafluoroethyl group, a 2-chloroethyl group, a 3-chloropropyl group and a 4-chlorobutyl group), C1-C5 alkoxy C1-C5 alkyl groups (such as a methoxymethyl group and a 2-methoxyethyl group), C1-C5 alkylthio C1-C5 alkyl groups (such as a methylthiomethyl group and a 2-methylthioethyl group), C1-C5 haloalkoxy C1-C5 alkyl groups (such as a 2,2,2-trifluoroethoxymethyl group), C1-C5 haloalkoxy C1-C5 haloalkyl groups, C1-C5 haloalkylthio C1-C5 alkyl groups (such as a 2,2,2-trifluoroethylthiomethyl group and the like), C1-C5 haloalkylthio C1-C5 haloalkyl groups, cyano C1-C5 alkyl groups (such as a cyanomethyl group, a 1-cyanoethyl group and a 2-cyanoethyl group), cyano C1-C5 haloalkyl groups, C1-C5 alkoxycarbonyl C1-C5 alkyl groups (such as a 1-(methoxycarbonyl)ethyl group and the like), C1-C5 alkyl groups having a C3-C8 alicyclic hydrocarbon group which optionally has halogen atoms and which optionally contains unsaturated bonds (such as a cyclopropylmethyl group, a cyclobutylmethyl group, a cyclopentylmethyl group and a cyclohexylmethyl group), or optionally substituted C7-C17 aralkyl groups (such as a benzyl group, an α-methylbenzyl group and an α,α-dimethylbenzyl group).

In Derivative (1), examples of the optionally substituted alkenyl group represented by X include C2-C10 alkenyl groups (such as a vinyl group, a 1-propenyl group, a 2-propenyl group, a 1-butenyl group, a 2-butenyl group and 3-butenyl group), and C2-C10 haloalkenyl groups (such as a 3,3,3-trifluoropropenyl group and a 1,1,2,3,3-pentafluoro-2-propenyl group and the like).

In Derivative (1), examples of the optionally substituted alkynyl group represented by X can include C2-C10 alkynyl groups (such as an ethynyl group, a propargyl group, a 2-butynyl group and a 3-butynyl group), or C2-C10 haloalkynyl groups (such as a 3,3,3-tetrafluoropropynyl group).

In Derivative (1), the optionally substituted phenyl group represented by X includes a phenyl group.

In Derivative (1), examples of the optionally substituted alkoxy group represented by X can include C1-C10 alkoxy groups (preferably C1-C5 alkoxy groups: such as a methoxy group, an ethoxy group, a propoxy group, a butoxy group, a pentyloxy group, an isobutoxy group, 2-methylbutoxy group and an isopentyloxy group), C1-C10 haloalkoxy groups (preferably C1-C5 haloalkoxy groups: such as a trifluoroethoxy group, a tetrafluoroethoxy group, a pentafluoroethoxy group, a tetrafluoropropoxy group, a 2-chloroethoxy group, a 3-chloropropoxy group and a 4-chlorobutoxy group); C1-C5 alkoxy C1-C5 alkoxy groups (such as a 2-methoxyethoxy group), C1-C5 alkylthio C1-C5 alkoxy groups (such as a 2-methylthioethoxy group and the like), C1-C5 haloalkoxy C1-C5 alkoxy groups (such as a 2,2,2-tetrafluoroethoxymethoxy group), C1-C5 haloalkoxy C1-C5 haloalkoxy groups, C1-C5 haloalkylthio C1-C5 alkoxy groups (such as a 2,2,2-trifluoroethylthiomethoxy group), C1-C5 haloalkylthio C1-C5 haloalkoxy groups, cyano C1-C5 alkoxy groups (such as a 2-cyanoethoxy group), C1-C5 alkoxycarbonyl C1-C5 alkoxy groups (such as a 2-(methoxycarbonyl)ethyl group), C1-C5 alkoxy groups having a C3-C8 alicyclic hydrocarbon group which optionally has halogen atoms and which optionally contains unsaturated bonds (such as a cyclopropylmethoxy group, a cyclobutylmethoxy group, a cyclopentylmethoxy group and a cyclohexylmethoxy group), or optionally substituted C7-C17 aralkyloxy groups (such as a benzyloxy group).

In Derivative (1), examples of the optionally substituted alkenyloxy group represented by X include e.g. C2-C10 alkenyloxy groups (preferably C2-C5 alkenyloxy groups: such as a 2-propenyloxy group, a 2-butenyloxy group, a 3-butenyloxy group and the like), or C2-C10 haloalkenyloxy groups (preferably C2-C5 haloalkynyloxy groups: such as a 2,3,3-tetrafluoro-2-propenyloxy group, 4,4,4-tetrafluoro-2-butenyloxy group, 2,3-difluoro-2-butenyloxy group, 2,4,4,4-tetrafluoro-2-butenyloxy group and the like).

In Derivative (1), the optionally substituted alkynyloxy group represented by X can include C2-C10 alkynyloxy groups (preferably C2-C5 alkynyloxy groups: such as a 2-propynyloxy group, a 2-butynyloxy group, a 3-butynyloxy group and the like), or C2-C10 haloalkynyloxy groups (preferably: C2-C5 haloalkynyloxy groups: such as a 4-chloro-2-butynyloxy group).

In Derivative (1), an example of the optionally substituted phenoxy group represented by X can include a phenoxy group.

In Derivative (1), the optionally substituted alkylthio group represented by X can include C1-C10 alkylthio groups (preferably C1-C5 alkylthio groups: such as a methylthio group, an ethylthio group, a propylthio group, a butylthio group, a pentylthio group, an isobutylthio group, a 2-methylbutylthio group and an isopentylthio group), C1-C10 haloalkylthio groups (preferably C1-C5 haloalkylthio groups: such as a trifluoroethylthio group, a tetrafluoroethylthio group, a pentafluoroethylthio group, a tetrafluoropropylthio group, a 2-chloroethylthio group, a 3-chloropropylthio group, a 4-chlorobutylthio group and the like), C1-C5 alkoxy C1-C5 alkylthio groups (such as a 2-methoxyethylthio group), C1-C5 alkylthio C1-C5 alkylthio groups (such as a 2-methylthioethylthio group), C1-C5 haloalkoxy C1-C5 alkylthio groups (such as a 2,2,2-tetrafluoroethoxymethylthio group), C1-C5 haloalkoxy C1-C5 haloalkylthio groups, C1-C5 haloalkylthio C1-C5 alkylthio groups (such as a 2,2,2-tetrafluoroethylthiomethylthio group), C1-C5 haloalkylthio C1-C5 haloalkylthio groups, cyano C1-C5 alkylthio groups (such as a 2-cyanoethylthio groups and the like), C1-C5 alkoxycarbonyl C1-C5 alkylthio groups (such as a 2-(methoxycarbonyl)ethylthio group), C1-C5 alkylthio groups having a C3-C8 alicyclic hydrocarbon group which optionally has halogen atoms and which optionally contains unsaturated bonds (such as a cyclopropylmethylthio group, a cyclobutylmethylthio group, a cyclopentylmethylthio group, a cyclohexylmethylthio group, a (1-cyclopentenyl)methylthio group, a (1-cyclohexenyl)methylthio group and the like), or optionally substituted C7-C17 aralkylthio groups (such as a benzylthio group).

In Derivative (1), examples of the optionally substituted alkenylthio group represented by X can include C2-C10 alkenylthio groups (preferably C2-C5 alkenylthio groups: such as a 2-propenylthio group, a 2-butenylthio group and a 3-butenylthio group), or C2-C10 haloalkenylthio groups (preferably C2-C5 haloalkenylthio groups: such as a 2,3,3-tetrafluoro-2-propenylthio group, a 4,4,4-tetrafluoro-2-butenylthio group, a 2,3-difluoro-2-butenylthio group and 2,4,4,4-tetrafluoro-2-butenylthio group).

In Derivative (1), the optionally substituted alkynylthio group represented by X includes e.g. C2-C10 alkynylthio groups (preferably C2-C5 alkynylthio groups: such as a 2-propenylthio group, a 2-butynylthio group and a 3-butynylthio group and the like), or C2-C10 haloalkynylthio groups (preferably C2-C5 haloalkynylthio groups).

In Derivative (1), examples of the optionally substituted phenylthio group represented by X can include optionally substituted phenylthio groups and the like.

In Derivative (1), examples of the optionally substituted alicyclic hydrocarbon group represented by X can include C3-C8 alicyclic hydrocarbon groups which optionally have halogen atoms and which optionally contain unsaturated bonds (such as a cyclopropyl group, a cyclobutyl group, a cyclopentyl group, a cyclohexyl group, a 1-cyclopentenyl group, a 2-cyclopentenyl group, a 3-cyclopentenyl group, a 1,3-cyclopentadienyl group, a 2,4-cyclopentadienyl group, a 1-cyclohexenyl group, a 2-cyclohexenyl group and a 3-cyclohexenyl group).

In Derivative (1), varieties of preferred substituents contained in X include C1-C5 alkyl groups, C1-C5 alkoxy groups, C1-C5 haloalkoxy groups, C2-C5 alkenyloxy groups, C2-C5 haloalkenyloxy groups, C2-C5 alkynyloxy groups, C2-C5 haloalkynyloxy groups, C1-C5 alkylthio groups, C1-C5 haloalkylthio groups, C2-C5 alkenylthio groups, C2-C5 haloalkenylthio groups, C2-C5 alkynylthio groups and C2-C5 haloalkynylthio groups.

In Derivative (1) used in the present invention, tautomers shown in the following formulae can exist, and Derivative (1) means a general term for all the tautomers.

Specific examples of preparation methods for a solution (2) include a method of reacting an alkali metal salt of a compound represented by the following formula (A) with a compound represented by the formula (A')

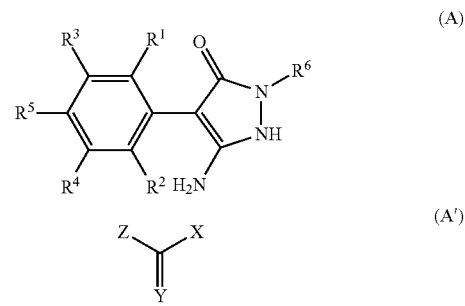

[wherein X and Y represent the same meanings as described above, and Z represents a halogen atom (such as a chlorine atom or a bromine atom)] in a good solvent to obtain a reaction mixture containing Derivative (1); a method of reacting an alkali metal salt of a compound represented by the following formula (B) with a compound represented by the following formula (B') in a good solvent to obtain a reaction mixture containing Derivative (1)

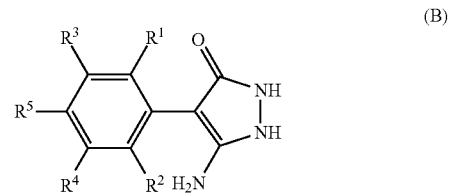

$R^6$-L (B'); a method of reacting an alkali metal salt of a compound represented by the formula (B) with a compound represented by the formula (A') in a good solvent to obtain a reaction mixture containing Derivative (1); and the like.

The reaction mixtures containing the Derivative (1) obtained by the preparation methods exemplified above are washed with an aqueous solution of a mineral acid such as an aqueous solution of hydrochloric acid or an aqueous solution of sulfuric acid, water and the like and the obtained solutions are preferred as the solution (2). Solutions washed with an

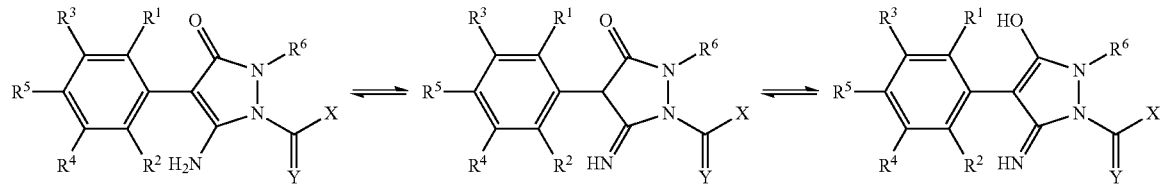

A solution (2) used in the present invention is a solution which may contain a good solvent which can dissolve Derivative (1) and the Derivative (1), and further unreacted materials, reaction byproducts and the like produced e.g. during production of the Derivative (1), and is preferably a reaction mixture obtained by preparing the Derivative (1) using a good solvent as a solvent.

aqueous solution of a mineral acid are preferably further washed with an aqueous solution containing a base such as sodium hydrogen carbonate, and water to neutralize.

Examples of a good solvent contained in a solution (2) include ether solvents such as 1,4-dioxane and tetrahydrofuran; ketone solvents such as methylisobutylketone; aromatic hydrocarbon solvents such as benzene, toluene and xylene; and the like.

In the method of the present invention, a good solvent is preferably an aromatic hydrocarbon solvent.

Derivative (1) contained in a solution (2) is dissolved completely. The content of the Derivative (1) in the solution (2) is approximately 1 to 50% by weight, and preferably 10 to 40% by weight.

In addition, the content of a good solvent in a solution (2) is approximately 50 to 99% by weight, and preferably 60 to 90% by weight.

A solution (2) may contain unreacted materials, reaction byproducts and the like produced e.g. during production of Derivative (1), but the total of the Derivative (1) and a good solvent in the solution (2) is preferably 90% by weight or more.

The method of the present invention comprises a step of mixing a solution (2) and a poor solvent to crystallize the above derivative (hereinafter may be referred as to the crystallization step).

As used herein, a poor solvent is a solvent wherein the solubility of Derivative (1) is lower than that of a good solvent, and which can be uniformly mixed with the good solvent. A poor solvent wherein the solubility of Derivative (1) is 1 g/100 ml or less is preferred.

Examples of a poor solvent to be used in the present invention include aliphatic hydrocarbon solvents such as n-heptane, 2-methylbutane, n-hexane and n-heptane; alicyclic hydrocarbon solvents such as cycloheptane, cyclohexane and 1-methylcycloheptane; solvents mixing two or more these solvents; and the like.

The temperature of a solution (2) to be used in the crystallization step is preferably 10° C. or more and less than the boiling point of a good solvent contained in the solution, and specifically preferably 20° C. to 90° C., and especially preferably 50° C. to 80° C.

Also, the temperature of a poor solvent used in the crystallization step is preferably in the temperature range of −50° C. or more and less than the boiling point of a good solvent contained in a solution (2) or the poor solvent, and specifically preferably −20° C. to 20° C.

Further, the temperature of a mixed liquid obtained by mixing a solution (2) and a poor solvent in the crystallization step is preferably in the temperature range of −50° C. or more and less than the boiling point of a good solvent contained in the solution (2) or the poor solvent, and specifically preferably −20° C. to 20° C.

The total amount of a solution (2) to be used for the crystallization step is preferably an amount of the solution (2) containing 11 to 50 parts by weight of Derivative (1) per 100 parts by weight of a poor solvent to be used in the crystallization step.

Specific examples of the crystallization step include a method of adding simultaneously a solution (2) and a poor solvent to one container, a method of adding a poor solvent to a solution (2), and a method of adding a solution (2) to a poor solvent. Every method is preferably carried out in a way of gradually adding them.

It is preferred that the crystallization step has a step of gradually adding a solution (2) to a poor solvent, and especially in the case of having the following first step to third step, it is preferred because the filterability of Derivative (1) to be obtained is good.

First step: a step of adding part of a solution (2) to a poor solvent to obtain a mixed liquid (1).
Second step: a step of crystallizing Derivative (1) contained in the mixed liquid (1) obtained in the first step to obtain a mixed liquid (2) containing crystals of the Derivative (1).
Third step: a step of further adding the remaining part of the solution (2) to the mixed liquid (2) obtained in the second step to crystallize the Derivative (1).

The first step is a step of adding part of a solution (2) to a poor solvent to obtain a mixed liquid (1).

In the first step, crystals of Derivative (1) may be deposited, however it is preferred that the temperature of the mixed liquid (1) be adjusted to a temperature at which the crystals are not deposited in terms of purity of the Derivative (1) to be obtained. The first step is, for example, preferably carried out at less than 40° C., and as the temperature of the mixed liquid (1) lowers, crystals of the Derivative (1) tend to be easily deposited.

An amount of part of a solution (2) to be used in the first step is preferably 1 to 10 parts by weight per 100 parts by weight of the total of the solution (2) to be used in the first step and the solution (2) to be used in the third step.

The second step is a step of crystallizing the Derivative (1) contained in the mixed liquid (1) obtained in the first step to obtain a mixed liquid (2) containing crystals of the Derivative (1), and can specifically include a step of crystallizing the Derivative (1) while the mixed liquid (1) obtained in the first step is maintained, for example, at less than 20° C., preferably the temperature range of −20° C. and 20° C.

It is preferred that in the second step the above temperature range be maintained until an amount of crystals to be deposited of the Derivative (1) contained in the mixed liquid (2) does not increase.

The time to maintain the temperature in the second step varies depending on maintaining temperature, and is preferably approximately for 10 minutes to 10 hours.

The third step is a step of further adding the remaining part of the solution (2) to the mixed liquid (2) obtained in the second step to crystallize the Derivative (1), and can specifically include a step of gradually adding the remaining part of the solution (2) to the mixed liquid (2) in order that the temperature of a mixture of the mixed liquid (2) and the remaining part of the solution (2) may be maintained at less than 40° C., preferably −20° C. to 20° C.

It is preferred that in the third step the above temperature range be maintained until an amount of crystals to be deposited of the Derivative (1) contained in the mixed liquid obtained in the third step does not increase.

The time to maintain the temperature in the third step varies depending on maintaining temperature, and is for 30 minutes to 10 hours, preferably approximately 1 to 8 hours.

In the crystallization step of the present invention, a retreat curve agitator, a flat retreat curve agitator, a pitched blade paddle impeller, a flat paddle impeller, a turbine, in the crystallization step of the present invention, Derivative (1) is preferably crystallized while stirring by a retreat curve agitator, a flat retreat curve agitator, a pitched blade paddle impeller, a flat paddle impeller, a flat-blade turbine, TWINSTIR (Trade Name, produced by Kobelco Eco-Solutions Co., Ltd.), an anchor impeller or the like. More preferably the crystallization step has the above first step to third step, and at least in the third step, Derivative (1) is crystallized while stirring by a retreat curve agitator, a flat retreat curve agitator, a pitched blade paddle impeller, a flat paddle impeller, a flat-blade turbine, TWINSTIR, an anchor impeller or the like.

The crystals of Derivative (1) obtained by the present invention can be easily isolated by separating using solid liquid separators such as Funda filter and a centrifuge. In addition, the obtained crystals can be further washed with water and an organic solvent, and can be further dried.

The crystals obtained by such methods, for example, contain 90% by weight of Derivative (1), and preferably 95% by weight of Derivative (1).

EXAMPLES

The present invention will now be described in more detail by way of examples thereof. Unless otherwise specified, the term "%" in Examples and comparative examples is percents by weight and parts by weight.

Example 1

Preparation of a Solution (2-1) Containing a Derivative (1-1) and a good solvent To a mixture of 24.8 g of 4-(2-methylphenyl)-5-amino-1H-pyrazol-3-one (131 mmol), 54 g of xylene and 12 g of water, 19.5 g of a 28% aqueous solution of sodium hydroxide (136 mmol) was added dropwise while stirring at room temperature (approximately 25° C.) to dissolve the solid content therein. To the obtained dissolved solution, 50 g of methanol was added, and the resulting mixture was cooled to 15° C., and to the mixture, 40.5 g of a xylene solution containing S-(2-propenyl)chlorothioformate at 50.5% (149.3 mmol) was added dropwise over 2 hours. At the same time as the addition, to the mixture, a 28% solution of sodium hydroxide was added dropwise to maintain pH around 11.5. At the completion of the addition, the amount used of the 28% aqueous solution of sodium hydroxide was 12.3 g (148.9 mmol). The mixture after the completion of the addition was maintained at 15° C. for 1 hour, and then heated to room temperature, followed by adding 46 g of 10% hydrochloric acid (126 mmol) to the mixture to adjust pH to 6. To the obtained mixture, 49 g of hexane was added dropwise while stirring at room temperature over 30 minutes, followed by stirring the mixture at room temperature for another 30 minutes. Then the obtained precipitate was filtered, and a wet cake of the retenate was washed with successively 50 g of hexane, and 50 g of a mixture, methanol: water=1:2. Next, in 150 g of the mixture, methanol: water=1:2, the washed wet cake was mixed, and the obtained mixture was filtered, and then a wet cake of the retenate was washed with 100 g of water. A separated wet cake was dried under reduced pressure by a vacuum pump at 50° C. over 12 hours until a constant weight was attained to obtain 33.31 g of 1-[(2-propenylthio)carbonyl]-4-(2-methylphenyl)-5-amino-1H-pyrazol-3-one (115.1 mmol).

$^1$H-NMR (CDCl$_3$)

δ(ppm): 7.20-7.28 (4H), 5.80-5.97 (1H), 5.49 (2H), 5.14-5.49 (2H), 3.61 (2H), 2.31 (3H).

To a mixed liquid of 119 kg of tetrahydrofuran (THF) and 238 kg of xylene, 140.7 kg of a water-wet cake containing 1-[(2-propenylthio)carbonyl]-4-(2-methylphenyl)-5-amino-1H-pyrazol-3-one at 84.9% (0.413 mol) was added and the obtained mixture was maintained around 50° C. to obtain a dissolved solution. The solution was washed twice with 60 kg of water to prepare a THF-xylene solution containing 1-[(2-propenylthio)carbonyl]-4-(2-methylphenyl)-5-amino-1H-pyrazol-3-one.

To another reactor, 18.2 kg of lithium hydroxide monohydrate (0.434 mol) and 239 kg of xylene were added, and then 7.1 kg of water distilled by heating to reflux under reduced pressure of 10 kPa was removed. To the reactor under reduced pressure while heating to reflux, the total amount of the above THF-xylene solution containing 1-[(2-propenylthio)carbonyl]-4-(2-methylphenyl)-5-amino-1H-pyrazol-3-one was added dropwise at a constant speed over 10.5 hours. Part of reflux liquid was removed from the above reactor. At the completion of the addition, the amount removed was 323 kg. After the completion of the addition, part of reflux liquid (39 kg) was removed over another 1 hour while heating to reflux.

Next, to the above reactor, 30 kg of xylene was added, and an operation to distill the same amount of distillate by simple distillation under reduced pressure of 10 kPa was repeated twice, and then an operation to separate water distilled by heating to reflux was carried out for 4 hours to prepare a xylene solution of lithium salt of 1-[(2-propenylthio)carbonyl]-4-(2-methylphenyl)-5-amino-1H-pyrazol-3-one.

Further, using another reactor, 358 kg of THF was heated to reflux at 65° C. under normal pressure, and then the total amount of the above xylene solution of lithium salt of 1-[(2-propenylthio)carbonyl]-4-(2-methylphenyl)-5-amino-1H-pyrazol-3-one and 124 kg of a xylene solution containing isopropyl mesylate at 55.6% (0.491 mol) were added dropwise concurrently over 1 hour. Next, the obtained mixture was heated to reflux at approximately 85° C. under normal pressure for 20 hours, and then the resulting mixture was cooled to 30° C. and adjusted to the reduced pressure of 15 kPa, and then the mixture was heated to distill 436 kg of a solvent by simple distillation. The obtained reaction mixture was dissolved in 388 g of xylene, and the obtained solution was washed with successively 239 kg of water, a caustic aqueous solution in which 15.6 kg of 25% sodium hydroxide was added to 239 kg of water, a dilute sulfuric acid in which 61 g of 20% sulfuric acid was added to 178 kg of water, and 239 kg of water at 50° C., and the obtained xylene solution was concentrated under reduced pressure of 10 kPa to obtain 315 kg of a xylene solution (solution 2-1) containing 1-[(2-propenylthio)carbonyl]-2-(1-methylethyl)-4-(2-methylphenyl)-5-amino-1H-pyrazol-3-one (derivative 1-1) at 35%.

(First Step)

In a 2 L of container equipped with a retreat curve agitator, 800 g of hexane was charged, and then the hexane was cooled to 5° C. Next, while stirring the hexane, 28 g of the solution (2-1) was added dropwise at approximately 5° C. over 1 hour. Precipitation of crystals was not found in the obtained mixed liquid.

(Second Step)

Using the same container in the first step, the obtained solution was stirred at approximately 5° C. for 2 hours, and precipitation of crystals was found.

(Third Step)

Using the same 2 L of container in the second step, to the solution containing crystals obtained in the second step while stirred at 570 rpm by a retreat curve agitator at approximately 5° C., 526 g of the solution (2-1) was added over 5 hours. The obtained mixture was stirred at approximately 5° C. for another 2 hours. In this case, the stirring power of the retreat curve agitator was 0.4 kW/m$^3$.

The obtained mixture was filtered to obtain 159 g of granulated substances wherein the main component was the derivative (1-1). In this case, the filterability was good.

The content of the derivative (1-1) contained in solids of the above granulated substances was 97% or more.

The measurement of the content of the derivative (1-1) contained in the solution (2-1) and the granulated substances was the results measured by the internal standard method of high performance liquid chromatography, and a measuring method according to JIS K-6828 was carried out for the above "solids of the granulated substances".

Example 2

First Step

In a container equipped with a retreat curve agitator, 800 g of hexane was charged, and then the hexane was cooled to 5° C. Next, to the hexane, 56 g of the solution (2-1) was added dropwise at the temperature over 1 hour.

Precipitation of crystals was not found in the obtained mixed liquid.

Second Step

Using the same container in the first step, the obtained solution was stirred at approximately 5° C. for 2 hours, and precipitation of crystals was found.

Third Step

Using the same 2 L of container in the second step, to the solution containing crystals obtained in the second step while stirred at 570 rpm by a retreat curve agitator at approximately 5° C., 500 g of the solution (2-1) was added over 2 hours. The obtained mixture was stirred at approximately 5° C. for another 2 hours. In this case, the stirring power of the retreat curve agitator was 0.4 kW/m$^3$.

The obtained mixture was filtered to obtain granulated substances wherein the main component was the derivative (1-1). In this case, the filterability was good.

The content of the derivative (1-1) contained in solids of the above granulated substances was 97% or more.

Example 3

To the solution of the second step obtained in the same manner as in Example 1, while stirred with a retreat curve agitator, 750 g of the solution (2-1) was added dropwise over 3 hours while maintaining at approximately 5° C. The obtained mixture was stirred at the same temperature for another 2 hours.

The content of the derivative (1-1) contained in solids of the above granulated substances was 97% or more.

Example 4

The third step was carried out according to Example 1 except stirring at a stirring speed of 670 rpm and a stirring power of 0.7 kW/m$^3$.

The obtained mixture was filtered to obtain granulated substances wherein the main component was the derivative (1-1). In this case, the filterability was good.

The content of the derivative (1-1) contained in solids of the above granulated substances was an equivalent result to that in Example 1.

Example 5

The third step was carried out according to Example 1 except stirring at a stirring speed of 360 rpm and a stirring power of 0.10 kW/m$^3$.

The obtained mixture was filtered to obtain granulated substances wherein the main component was the derivative (1-1). In this case, the filterability was good.

The content of the derivative (1-1) contained in solids of the above granulated substances was an equivalent result to that in Example 1.

INDUSTRIAL APPLICABILITY

By the present invention, the above pyrazolinone derivative represented by the formula (1) can be industrially easily purified.

The invention claimed is:

1. A method for purifying a pyrazolinone compound, wherein the pyrazolinone compound is 1-[(2-propenylthio)carbonyl]-2-(1-methylethyl)-4-(2-methylphenyl)-5-amino-1H-pyrazol-3-one, comprising a step of adding a solution containing a mixture containing the pyrazolinone compound and a good solvent which can dissolve the pyrazolinone derivative to a poor solvent and crystallizing the pyrazolinone compound at −20° C. to 20° C., wherein the good solvent is xylene, and the poor solvent is hexane, and wherein 1 to 50 parts by weight of the pyrazolinone compound is added per 100 parts by weight of the poor solvent.

2. A method for purifying a pyrazolinone compound, wherein the pyrazolinone compound is 1-[(2-propenylthio)carbonyl]-2-(1-methylethyl)-4-(2-methylphenyl)-5-amino-1H-pyrazol-3-one, the method comprising the following first step to third step;

First step: a step of adding part of a solution containing a mixture containing the pyrazolinone compound and a good solvent which can dissolve the pyrazolinone compound to a poor solvent to obtain a mixed liquid (1), Second step: a step of crystallizing at −20° C. to 20° C. the pyrazolinone compound contained in the mixed liquid (1) obtained in the first step to obtain a mixed liquid (2) containing crystals of the derivative, and Third step: a step of further adding the remaining part of said solution to the mixed liquid (2) obtained in the second step and crystallizing the pyrazolinone compound at −20° C. to 20° C., wherein the good solvent is xylene, and the poor solvent is hexane, and wherein 1 to 50 parts by weight of the pyrazolinone compound is added per 100 parts by weight of the poor solvent.

3. The purifying method according to claim 2, wherein an amount of said solution to be used in the first step is 1 to 10 parts by weight per 100 parts by weight of the total of said solution to be used in the first step and said solution to be used in the third step.

4. The purifying method according to claim 1, wherein the crystallization is carried out while stirring by a retreat curve agitator at a required power of 0.05 to 0.7 kW/m$^3$.

5. The purifying method according to claim 2, wherein the crystallization is carried out while stirring by a retreat curve agitator at a required power of 0.05 to 0.7 kW/m$^3$ in the third step.

* * * * *